(12) United States Patent
Nagireddy et al.

(10) Patent No.: US 12,347,556 B2
(45) Date of Patent: Jul. 1, 2025

(54) SYSTEMS AND METHODS FOR INTEGRATING A GLOBALLY SECURE COMMUNICATIONS NETWORK WITH STORED MEDICAL DIAGNOSTICS

(71) Applicant: TeleTracking Technologies, Inc., Pittsburgh, PA (US)

(72) Inventors: Sunil Nagireddy, Pittsburgh, PA (US); Vipul Sinha, Pittsburgh, PA (US); Prashant Kumar, Bangalore Karnataka (IN)

(73) Assignee: TeleTracking Technologies, Inc., Pittsburgh, PA (US)

( * ) Notice: Subject to any disclaimer, the term of this patent is extended or adjusted under 35 U.S.C. 154(b) by 91 days.

(21) Appl. No.: 16/235,093

(22) Filed: Dec. 28, 2018

(65) Prior Publication Data
US 2020/0135335 A1 Apr. 30, 2020

(51) Int. Cl.
*G16H 50/20* (2018.01)
*G16H 80/00* (2018.01)
*H04L 9/40* (2022.01)

(52) U.S. Cl.
CPC .............. *G16H 50/20* (2018.01); *G16H 80/00* (2018.01); *H04L 63/08* (2013.01)

(58) Field of Classification Search
CPC ......... G16H 80/00; G16H 50/20; H04L 63/08
See application file for complete search history.

(56) References Cited

U.S. PATENT DOCUMENTS

| 9,918,191 B2 * | 3/2018 | Baca ...................... H04W 4/021 |
| 2005/0182661 A1 * | 8/2005 | Allard ................. G06F 21/6245 705/3 |
| 2012/0303827 A1 * | 11/2012 | Neystadt ............. G06F 21/6218 709/229 |

(Continued)

FOREIGN PATENT DOCUMENTS

KR 10-1992301 B1 * 1/2018

OTHER PUBLICATIONS

Prey software secures mobile device fleets for 21 new hospital and health care customers: Health care industry turns to prey anti-theft to lock down mobile devices; geofencing control zones empower location-aware device security. (Feb. 5, 2018). NASDAQ OMX's News Release Distribution Channel Retriev (Year: 2018).*

*Primary Examiner* — Sheetal R Paulson
(74) *Attorney, Agent, or Firm* — FERENCE & ASSOCIATES LLC

(57) ABSTRACT

The present disclosure relates to systems and methods for integrating a globally secure communications network with stored medical diagnostics. In one example, the system may include at least one memory storing instructions and at least one processor configured to execute the instructions. The instructions may include instructions to receive a request for a medical diagnostic; verify that the request originates from a location within an approved area; verify credentials of a user that originated the request; send the medical diagnostic to the user; receive, from the user, an identification of a recipient separate from the user; verify that the recipient originates from a location within an approved area; verify credentials of a user that originated the request; and in response to receiving the identification, send the medical diagnostic to the recipient.

20 Claims, 5 Drawing Sheets

(56) References Cited

U.S. PATENT DOCUMENTS

| | | | | |
|---|---|---|---|---|
| 2013/0103423 A1* | 4/2013 | Kim | ................ | G06Q 10/00 |
| | | | | 705/3 |
| 2014/0358574 A1* | 12/2014 | Tara | ................ | G01S 5/02 |
| | | | | 705/2 |
| 2016/0301691 A1* | 10/2016 | Miller | ................ | G01S 5/14 |
| 2019/0364381 A1* | 11/2019 | Weston | ................ | H04W 4/40 |

* cited by examiner

SYSTEMS AND METHODS FOR INTEGRATING A GLOBALLY SECURE COMMUNICATIONS NETWORK WITH STORED MEDICAL DIAGNOSTICS

PRIORITY CLAIM

This application claims priority to Indian Application No. 201811040848, filed Oct. 29, 2018, which is hereby incorporated by reference in its entirety.

TECHNICAL FIELD

The present disclosure relates generally to the field of secure communications. More specifically, and without limitation, this disclosure relates to systems and methods for providing a globally secure communications network for transmitting and receiving stored medical diagnostics.

BACKGROUND

Medical information (or "diagnostics"), such as heartbeat measurements, X-ray images, CT scans, or the like, are generally subject to privacy laws and regulations. For example, the United States requires that medical information be kept confidential under the Health Insurance Portability and Accountability Act. By way of further example, the European Union has similar requirements under the Privacy Directive.

Such privacy requirements can make communication between caregivers difficult. For example, caregivers are subject to numerous strict requirements when sending text messages to each other. By way of further example, storage and transmission of digital copies of medical information are also subject to numerous strict requirements. Digital copies of medical information may be shared electronically by industry accepted secured protocols such as HTTPS or TLS. The electronic sharing may be conducted in conjunction with user authentication so that the data is shared between two or more intended users.

SUMMARY

In view of the foregoing, embodiments of the present disclosure describe systems and methods for integrating a secure communications network with stored medical diagnostics. The provided systems may use geofencing, single sign-on (SSO), and/or other global security mechanism to provide a secure and private communication channel between caregivers. Accordingly, the channel provided herein may be compliant with privacy laws and regulations as well as providing assurance to a patient that personal information is not being exposed.

In one embodiment, the present disclosure describes a system for integrating a globally secure communications network with stored medical diagnostics. The system may comprise at least one memory storing instructions and at least one processor configured to execute the instructions. The instructions may comprise instructions to receive a request for a medical diagnostic; verify that the request originates from a location within an approved area; verify credentials of a user that originated the request; send the medical diagnostic to the user; receive, from the user, an identification of a recipient separate from the user; verify that the recipient originates from a location within an approved area; verify credentials of a user that originated the request; and in response to receiving the identification, send the medical diagnostic to the recipient.

In another embodiment, the present disclosure describes a method for integrating a globally secure communications network with stored medical diagnostics. The method may be executed on one or more processors. The method may comprise receiving a request for a medical diagnostic; verifying that the request originates from a location within an approved area; verifying credentials of a user that originated the request; sending the medical diagnostic to the user; receiving, from the user, an identification of a recipient separate from the user; verifying that the recipient originates from a location within an approved area; verifying credentials of a user that originated the request; and in response to receiving the identification, sending the medical diagnostic to the recipient.

In a third embodiment, the present disclosure describes a system for automatically updating a plurality of caregivers over a globally secure communications network. The system may comprise at least one memory storing instructions and at least one processor configured to execute the instructions. The instructions may comprise instructions to receive a medical diagnostic associated with a patient having a plurality of caregivers; verify, using devices associated with the plurality of caregivers, that locations associated with the plurality of caregivers; verify credentials of the plurality of caregivers; automatically transmit an update including the medical diagnostic to verified caregivers; and withhold the update from caregivers that were not verified.

In a fourth embodiment, the present disclosure describes a method for automatically updating a plurality of caregivers over a globally secure communications network. The method may be executed on one or more processors. The method may comprise receiving a medical diagnostic associated with a patient having a plurality of caregivers; verifying, using devices associated with the plurality of caregivers, that locations associated with the plurality of caregivers; verifying credentials of the plurality of caregivers; automatically transmitting an update including the medical diagnostic to verified caregivers; and withholding the update from caregivers that were not verified.

In additional embodiments, the present disclose describes non-transitory, computer-readable media for causing one or more processors to execute methods consistent with the present disclosure.

It is to be understood that the foregoing general description and the following detailed description are example and explanatory only and are not restrictive of the disclosed embodiments.

BRIEF DESCRIPTION OF THE DRAWINGS

The accompanying drawings, which comprise a part of this specification, illustrate several embodiments and, together with the description, serve to explain the principles disclosed herein. In the drawings.

DETAILED DESCRIPTION

Figure 1:
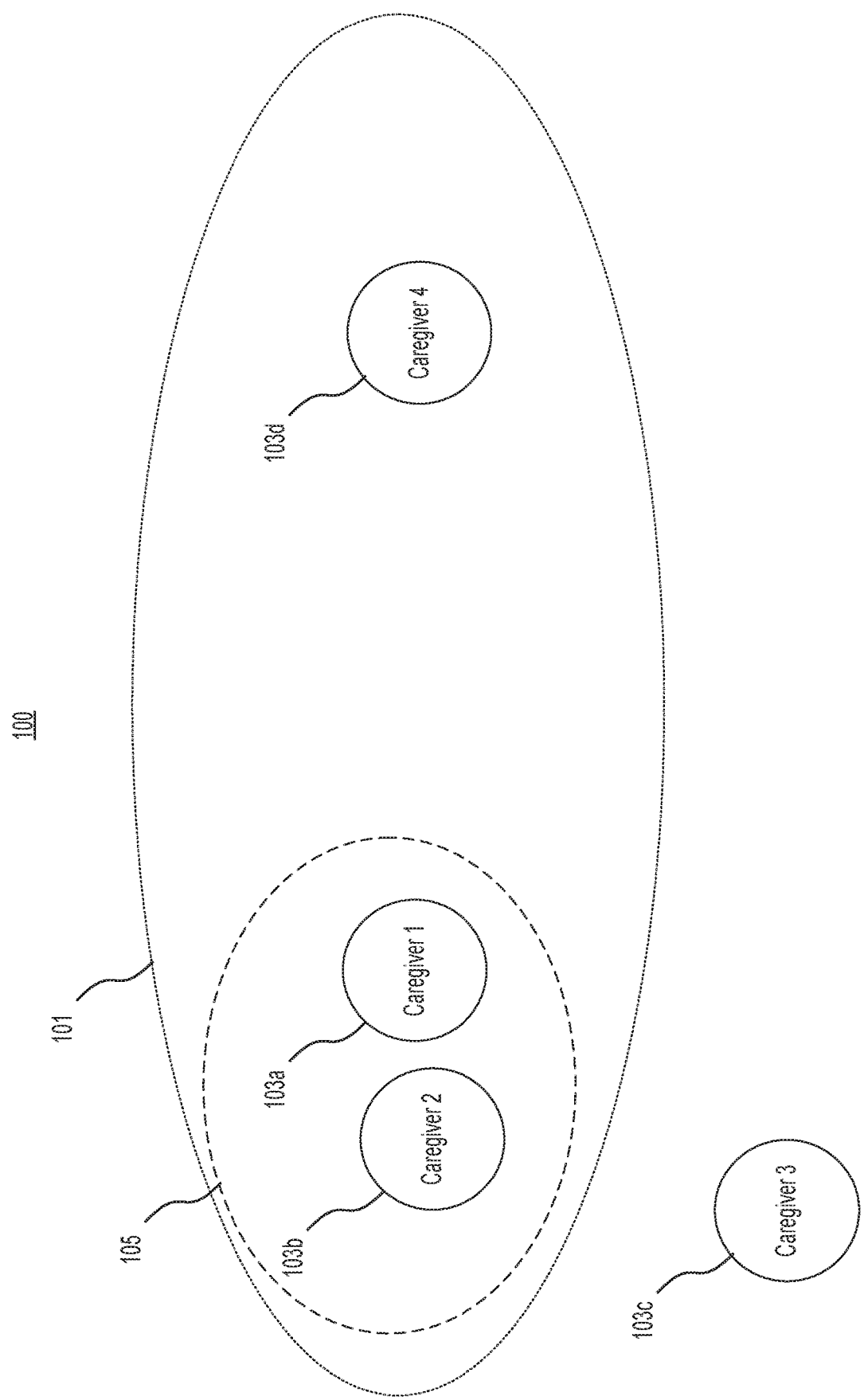
FIG. 1 is a block diagram of caregivers within a secured communications network, according to an example embodiment of the present disclosure.

The disclosed embodiments relate to systems and methods for integrating a globally secure communications network with stored medical diagnostics. Embodiments of the present disclosure may be implemented using a general-purpose computer. Alternatively, a special-purpose computer may be built according to embodiments of the present disclosure using suitable logic elements.

Advantageously, disclosed embodiments may provide a secure and confidential communications network between caregivers. Accordingly, communications between and updates sent to caregivers may be compliant with relevant privacy laws and regulations as well as secure in the eyes of the customer.

According to an aspect of the present disclosure, a user may request one or more pieces of medical information (referred to herein as "medical diagnostics") that are stored remotely from the user. For example, the user may comprise a caregiver (such as a doctor, nurse, surgeon, or the like) and may send the request using a user interface device such as a smartphone, tablet, laptop, or the like. The request may be sent over one or more computer networks, such as the Internet, a local area network (LAN), or the like, and may be sent using WiFi, 4G, Ethernet, or the like. In some embodiments, to retain security, the request may be sent over a private network (such as a LAN) and may be encrypted (e.g., using an Advanced Encryption Standard (AES)).

In response to the request, one or more processors controlling access to the stored medical diagnostic may receive the request and verify a location of the user, for example, by verifying a location of the user interface device from which the request originated. The verification may use global positioning system (GPS) coordinates or other data indicative of location received from the user interface device, an internet protocol (IP) address or other data indicative of a location of the user interface device on the computer network, or the like. For example, credential-based authentication, and role-based authorization may be used to share the stored medical diagnostic. Users are not necessarily required to be within the same network, vicinity, or geography. Accordingly, users and/or recipients may be in separate or different networks, vicinities, or geographies. In another example, a medical campus may be geofenced such that only devices within the campus may submit requests. The "geofencing" may exist by virtue of a LAN or other private network such that the ability to access the private network may serve as verification of the location of the user. In other embodiments, the "geofencing" may exist independently of the private network.

In some embodiments, the credential-based authentication, and role-based authorization may be used to share the stored medical diagnostic. In a non-limiting example, the credential-based authentication, and role-based authorization may be implemented in a smart mobile device such as an iOs based device such as an iPhone, iPod Touch, or an iPad, or an Android based device capable of hosting applications for implementing the credential-based authentication and the role-based authentication. In some embodiments, the geofencing may be include at least a portion that is mobile. For example, the geofence may include one or more emergency transport vehicles. Accordingly, the vehicles and the vicinity of the vehicles may comprise approved locations for users. As used herein, "vicinity" refers to a predetermined distance, such as 10 feet, 20 yards, or the like, or to a dynamic distance, such as 50 feet when the vehicle is stopped but 20 feet when the vehicle is in motion. A dynamic distance may be motion-dependent, speed-dependent, location-dependent, or the like. In such embodiments, the one or more processors may receive or access locations of the vehicles in order to verify the location of the user.

The one or more processors may also verify the credentials of the user originating the request. For example, the user may submit a username and password, one or more biometrics, retina scans, facial identification recognition, or other credentials with the request. In some embodiments, the one or more processors may use a single sign-on procedure such that a user logged into, for example, the LAN or other private network may have their credentials automatically sent to the one or more processors from a Lightweight Directory Access Protocol (LDAP). In other embodiments, the request may be sent from a pre-authorized application on the user interface device, and the application may use the pre-authorization to automatically send credentials with the request.

When the user is verified using location and credentials, the one or more processors may transmit the requested medical diagnostic to the user (e.g., via the user interface device). Similar to the request, the medical diagnostic may be sent over one or more computer networks, such as the Internet, a LAN, or the like, and may be sent using WiFi, 4G, Ethernet, or the like. In some embodiments, to retain security, the request may be sent over a private network (such as a LAN) and may be encrypted (e.g., using an Advanced Encryption Standard (AES)). The security may be retained over the network with the use of the Wireless Communications Transfer protocol (WCTP) in conjunction with Transport Layer Security (TLS) when communicating over the network(s).

The user who has received a medical diagnostic may wish to share the medical diagnostic with another user (e.g., a fellow caregiver). According to an aspect of the present disclosure, a user may send an identification (e.g., email address, user name, phone number, etc.) of one or more recipients for one or more pieces of the medical diagnostic. For example, the user may select one or more contacts on a user interface device as recipients. In embodiments where the user interface device runs a pre-authorized application, the application may automatically identify a list of fellow caregivers and/or potential caregivers based on a patient associated with the medical diagnostic.

Similar to the request, the identification may be sent over one or more computer networks, such as the Internet, a LAN, or the like, and may be sent using WiFi, 4G, Ethernet, or the like. In some embodiments, to retain security, the identification may be sent over a private network (such as a LAN) and may be encrypted (e.g., using an Advanced Encryption Standard (AES)).

The system may perform the same verifications above to ensure that the request to share the medical diagnostic is approved. For example, as with the request above, the one or more processors controlling access to the stored medical diagnostic may verify a location of the user, for example, by verifying a location of the user interface device from which the request originated. In addition, the one or more processors may also verify the credentials of the user originating the request.

In some embodiments, the same verifications may be performed on the recipient. For example, before sharing the medical diagnostic, the one or more processors controlling access to the stored medical diagnostic may verify a location of the recipient, for example, by verifying a location of a user interface device associated with the recipient. In such embodiments, the user must be within the approved area (such as a medical campus, the vicinity of an emergency transport vehicle, or the like) as well as the recipient for the sharing to be successfully executed.

Additionally, or alternatively, the one or more processors may also verify the credentials of the recipient. For example, the recipient may only be approved to view certain types of medical diagnostics (e.g., X-ray images), medical diagnostics associated with particular patients, or the like. In some embodiments, the one or more processors may request credentials from the recipient prior to sharing the medical diagnostic. For example, the one or more processor may request a username and password, one or more biometrics, or other credentials of the recipient. In some embodiments, the one or more processors may use a single sign-on procedure such that a recipient logged into, for example, the LAN or other private network may have their credentials automatically pulled from a Lightweight Directory Access Protocol (LDAP). In other embodiments, the recipient may have a pre-authorized application on a user interface device associated with the recipient, and the application may use the pre-authorization to send credentials in response to a request from the one or more processors.

By using combinations of verification of location and/or credentials of a user and/or a recipient, systems of the present disclosure may prevent the transmission of sensitive and private medical information to non-authorized parties. Moreover, systems of the present disclosure may prevent recipients from receiving and viewing medical diagnostics outside of an approved area, such as a medical campus. Additionally, or alternatively, there may be a plurality of approved areas within a medical campus.

In a related embodiment, a system storing medical diagnostics may receive a new medical diagnostic associated with a patient. For example, an X-ray image, CT scan, heartbeat monitor, or other output of a medical device and/or test may be send to the system for storage. Based on the associated patient, the system may determine one or more caregivers associated with that patient. For example, a patient identified as patient #14687 (or by some other identifier) may be associated with a nurse who is caring for them, a head nurse for the floor on which they are staying, a surgeon who has performed and/or will perform one or more surgeries on the patient, an attending physician, a primary care physician, one or more experts, or the like.

One or more processors of the system may, in response to receiving the new medical diagnostic, verify locations of the plurality of caregivers associated with the patient, as explained above. Additionally, or alternatively, the one or more processor may, in response to receiving the new medical diagnostic, verify credentials of the plurality of caregivers associated with the patient, as explained above.

Accordingly, the one or more processors may then generate an update including the new medical diagnostic. For example, the update may comprise a chat message including the new diagnostic (or a link to view the new diagnostic) sent to an application on user interface devices associated with the plurality of caregivers. The application may be configured to receive encrypted chat messages and therefore preserve the secrecy of the medical diagnostic being transmitted. By way of further example, the update may comprise a push notification for the user interface devices. The push notification may hide sensitive information until the caregiver unlocks the associated user interface device. For example, the push notification may simply state, "A patient has a new X-ray image" or "There is new information about a patient." Such notifications may preserve the secrecy of the medical diagnostic in case others view a lock screen of a user interface device associated with a caregiver.

In embodiments having links to the medical diagnostic and/or hidden information, the one or more processors may require verification of the credentials of the caregiver prior to displaying or transmitting the medical diagnostic and/or hidden information. By requiring credentials prior to displaying or transmitting the full medical diagnostic, the one or more processors may allow for transmitting an update without sensitive information to all caregivers (or all caregivers within the approved location) associated with the patient without having to first authenticate the credentials of each caregiver. Accordingly, the system may send updates more quickly and only authenticate caregivers on an on-demand basis, which reduces the chance of resource bottlenecks and delayed updates. Alternatively, the one or more processors may require credentials prior to displaying or transmitting the full medical diagnostic as a second authentication procedure. Accordingly, the one or more processor may authenticate a caregiver twice, once while sending the update and once while revealing the full medical diagnostic, in order to increase the security of the system.

The one or more processors may therefore transmit the update to verified caregivers and withhold the update from non-verified caregivers. In some embodiments, caregivers that do not receive the update may need to access the new medical diagnostic manually. In other embodiments, caregivers that do not receive the update when the new medical diagnostic is stored may receive the update when they become verified. For example, the one or more processors may retain a list of non-verified caregivers, monitor locations and/or credentials of the non-verified caregivers, and transmit the update to a caregiver when the caregiver goes from non-verified to verified status.

In embodiments where the location of the caregiver precluded verification, the caregiver may receive the update after entering an approved location. For example, an application on the user interface device may request updates periodically and/or whenever the caregiver enters the approved area. Additionally, or alternatively, the one or more processors may periodically request a location of the caregiver and attempt verification. In embodiments where the credentials of the caregiver precluded verification, the caregiver may receive the update after entering credentials, e.g., manually or by logging onto a private network. For example, the caregiver may log into an application on the user interface device, which may then request updates after successfully authenticating the caregiver. Additionally, or alternatively, the one or more processors may periodically request credentials from the caregiver and attempt verification.

To preclude stale updates, the retained list may have an expiry date and/or time. For example, the one or more processors may indicate that the list is to expire on Tuesday, October $2^{nd}$, or may indicate that the list is to expire in one day. After the list expires, the one or more processors may no longer transmit updates including the new medical diagnostic. Additionally, or alternatively, the one or more processors may stop transmitting updates when the patient associated with the new medical diagnostic is discharged from the hospital.

Accordingly, systems of the present disclosure may quickly and efficiently update all associated caregivers of the new medical diagnostic. Moreover, they may do so in a safe and secure manner to prevent the transmission of sensitive and private medical information to non-authorized parties and prevent caregivers from receiving updates with sensitive medical information outside of an approved area, such as a medical campus.

In another related embodiment, a first application on a user interface device may engage in secure inter-application communications with a second application on the user interface device. For example, the first application may have one or more medical diagnostics, and the second application may request at least one medical diagnostic from the first application. In such an example, the second application may use an application programming interface (API) call to the first application for the at least one medical diagnostic. The first application may request authentication from the second application, and the second application may provide one or more credentials. Additionally, or alternatively, the second application may provide credentials with the request. For example, the first application and the second application may use the same credentials (such as a username and password, at least one biometric, or the like). In another example, the first application and the second application may use different credentials that are linked such that credentials from the first application may be used to authenticate the user in the second application, and/or vice versa. Additionally, or alternatively, the first application may (e.g., at the request of the user) send at least one medical diagnostic to the second application.

Upon receipt of the at least one medical diagnostic, the second application may allow a user to submit a request to transmit the at least one medical diagnostic to one or more recipients. In some embodiments, the second application may receive or access a list of users associated with a patient that is associated with the medical diagnostic. For example, the second application may send a request for the list to a remote server. Concurrently with or separately from the request, the second application may send information such as a location of the user device, one or more credentials of the user, or combinations thereof, to the remote server in order to verify the user, as explained above. Upon receipt of the list of users associated with the patent, the second application may generate a graphical user interface displaying the list to the user. The user may then select the one or more recipients from the list of associated users.

To effectuate the transmission, the first application may submit information such as a location of the user device, one or more credentials of the user, or combinations thereof, to a remote server along with a request to transmit the at least one medical diagnostic. For example, the request, the location, and/or the credentials may be sent using one or more computer networks, such as the Internet, a LAN, or the like, and may be sent using WiFi, 4G, Ethernet, or the like. In some embodiments, to retain security, the request, the location, and/or the credentials may be sent over a private network (such as a LAN) and may be encrypted (e.g., using an Advanced Encryption Standard (AES)). The remote server may then operate as explained above to verify the request and transmit the at least one medical diagnostic.

In FIG. 1, there is shown a block diagram of a system 100 of caregivers (e.g., caregivers 103a, 130b, 103c, and 103d) within a secured communications network. As depicted in FIG. 1, an approved area 100 may comprise a single area, such as a medical campus. Additionally, or alternatively, approved area 100 may include one or more separate areas, such as satellite campuses, and/or one or more mobile areas, such as emergency vehicles. The vicinities of campuses and/or vehicles may be included in approved area 100.

As further depicted in FIG. 1, caregivers 103a, 130b, and 103d are within approved area 100. Accordingly, in embodiments where location is verified, caregivers 103a, 130b, and 103d may be verified to send medical diagnostics to and received medical diagnostics from each other. Similarly, in such embodiments, caregivers 103a, 130b, and 103d may receive updates about new medical diagnostics, as described above.

As depicted in FIG. 1, caregivers 103a and 103b are within team 105. For example, caregivers 103a and 103b may both care for a particular patient while caregivers 103c and 103d do not. Accordingly, in embodiments where credentials are verified, caregivers 103a and 103b may be verified to send medical diagnostics to and received medical diagnostics from each other at least with regards to the particular patient. Similarly, in such embodiments, caregivers 103a, 130b, and 103d may receive updates about new medical diagnostics associated with the particular patient, as described above. On the other hand, caregivers 103c and 103d would not be verified to send medical diagnostics to and received medical diagnostics from each other at least with regards to the particular patient and would not be verified to receive updates about new medical diagnostics associated with the particular patient.

Accordingly, as depicted in FIG. 1, information about patients may be protected both from distribution beyond the campus(es) and/or vehicle(s) as well as from distribution to caregivers that are not associated with a particular patient.

Figure 2A:
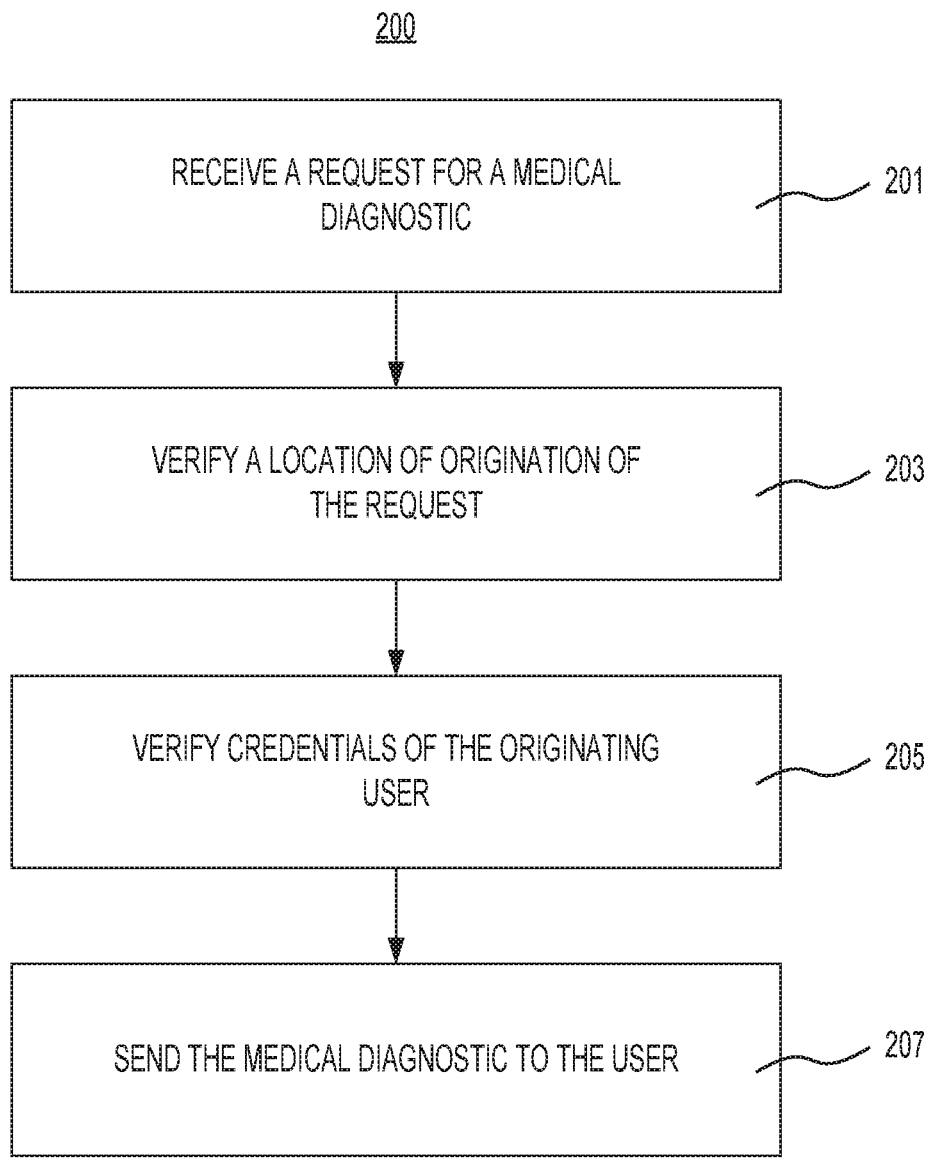
FIG. 2A is a flowchart of a first part of an example method for integrating a globally secure communications network with stored medical diagnostics, according to an example embodiment of the present disclosure.
Figure 2B:
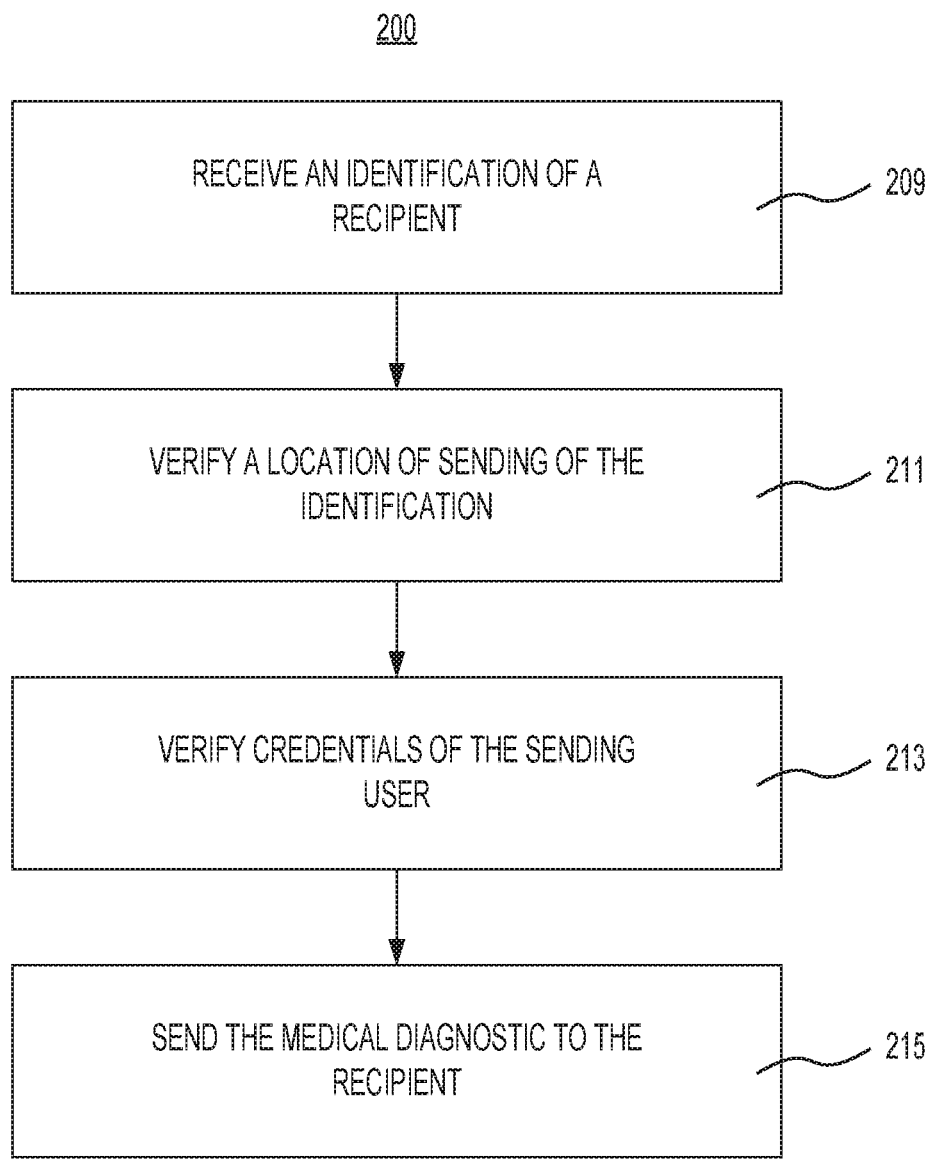
FIG. 2B is a flowchart of a second part of an example method for integrating a globally secure communications network with stored medical diagnostics, according to an example embodiment of the present disclosure.

FIGS. 2A and 2B depict an example method 200 for integrating a globally secure communications network with stored medical diagnostics. Method 200 may be implemented using one or more processors (e.g., processor 403 of FIG. 4).

At step 201, the processor may receive a request for a medical diagnostic. As explained above, the request may originate from a user via an associated user interface device. The user may comprise a caregiver (such as a doctor, nurse, surgeon, or the like), and the user interface device may comprise a smartphone, tablet, laptop, or the like. The request may be received over one or more computer networks, such as the Internet, a LAN, or the like, and may be sent using WiFi, 4G, Ethernet, or the like. In some embodiments, to retain security, the request may be received over a private network (such as a LAN) and may be encrypted (e.g., using an Advanced Encryption Standard (AES)). In such embodiments, the processor may decrypt the request, for example, using an appropriate private key.

At step 203, the processor may be within the destination's network and may verify that the request originates from a location within an approved area. For example, as explained above, the processor may receive data indicative of a location of the user interface device. The data indicative of the location may be sent separately from or together with the request. The data indicative of the location may be encrypted or sent unencrypted. If encrypted, the processor may decrypt the request, for example, using an appropriate private key.

At step 205, the processor may verify credentials of a user that originated the request. For example, as explained above, the processor may receive a username and password, at least one biometric, or other data that may be used to authenticate the user. Alternatively, or additionally, the processor may receive data used to authenticate the user using a single sign-on process. The data used to authenticate the user may be sent separately from or together with the request and/or the location. The data used to authenticate the user may be encrypted or sent unencrypted. If encrypted, the processor may decrypt the request, for example, using an appropriate private key.

At step 207, the processor may send the medical diagnostic to the user (or to the user interface device associated with the user). For example, the medical diagnostic may be sent over one or more computer networks, such as the Internet, a LAN, or the like, and may be sent using WiFi, 4G, Ethernet, or the like. In some embodiments, to retain security, the request may be received over a private network (such as a LAN). The network may be the same network used to receive the request, the location, and/or the data used to authenticate the user or may be a different network. In some embodiments, the medical diagnostic may be encrypted (e.g., using an Advanced Encryption Standard (AES)). In such embodiments, the user interface device may decrypt the diagnostic, for example, using an appropriate private key.

At step 209, the processor may receive, from the user, an identification of a recipient separate from the user. For example, the identification may comprise an email address, a username, a phone number, or the like. As explained above, the user may select one or more contacts on a user interface device as recipients. Alternatively, or concurrently, the user interface device may use a pre-authorized application that may automatically identify a list of fellow caregivers and/or potential caregivers based on a patient associated with the medical diagnostic.

At step 211, the processor may verify that the identification was sent from a location within an approved area. For example, step 211 may be performed similarly to step 203, described above.

At step 213, the processor may verify credentials of a user that originated the request. For example, step 213 may be performed similarly to step 205, described above.

At step 215, in response to receiving the identification, the processor may send the medical diagnostic to the recipient. For example, the medical diagnostic may be sent over one or more computer networks, such as the Internet, a LAN, or the like, and may be sent using WiFi, 4G, Ethernet, or the like. In some embodiments, to retain security, the request may be received over a private network (such as a LAN). The network may be the same network used to receive the request, the location, and/or the data used to authenticate the user, may be the same network used to send the medical diagnostic to the user, or may be a different network. In some embodiments, the medical diagnostic may be encrypted (e.g., using an Advanced Encryption Standard (AES)). In such embodiments, a user interface device associated with the recipient may decrypt the diagnostic, for example, using an appropriate private key.

Method 200 may include additional steps. For example, method 200 may further include verifying credentials of the recipient. The processor may verify the credentials of the recipient similarly to the verification of the credentials of the user.

By way of further example, method 200 may include verifying that the recipient has an associated location within the approved area. The processor may verify the associated location of the recipient similarly to the verification of the location of the user.

Figure 3:
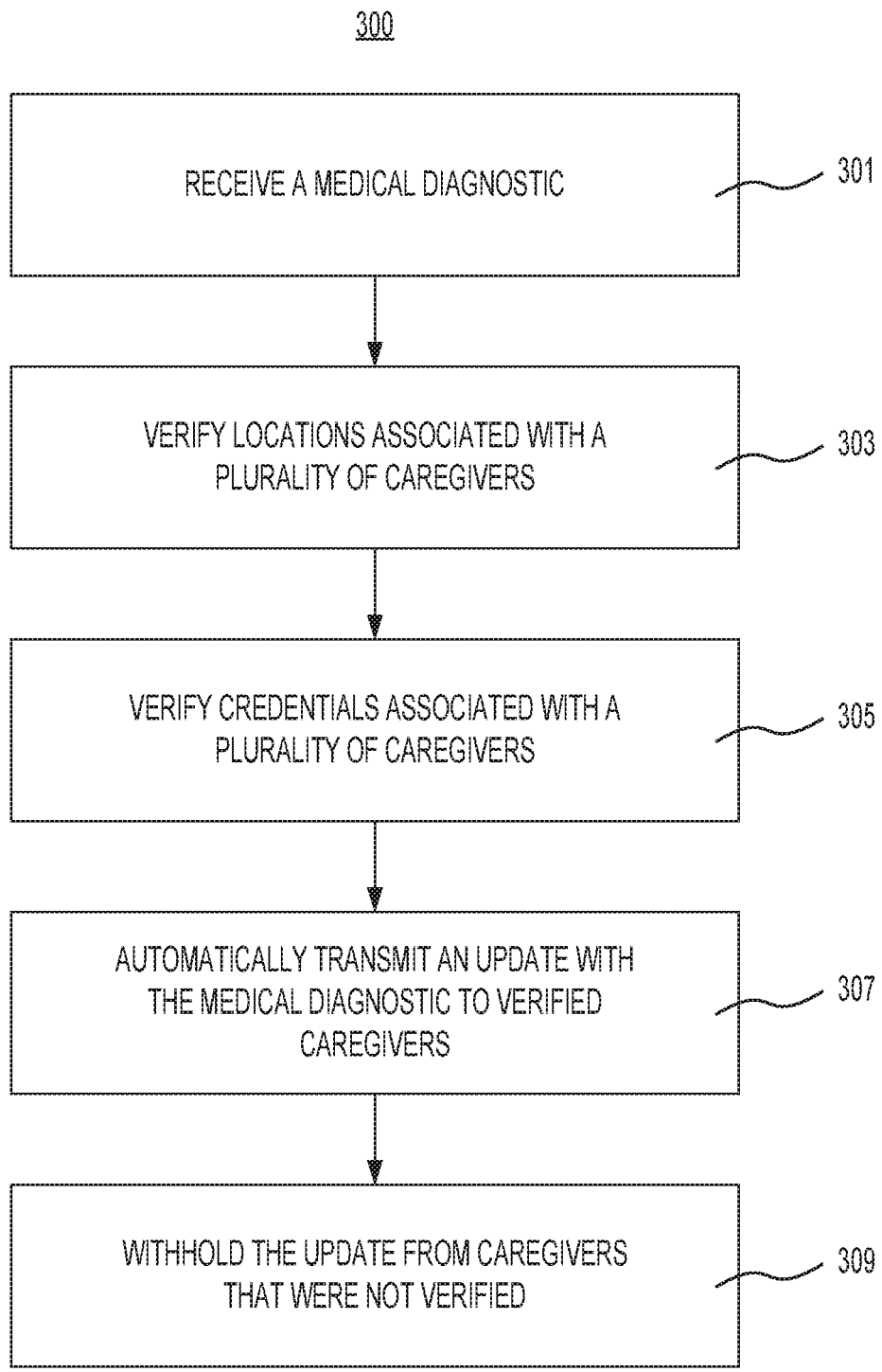
FIG. 3 is a flowchart of an example method for automatically updating a plurality of caregivers over a globally secure communications network, according to an example embodiment of the present disclosure.

FIG. 3 depicts an example method 300 for automatically updating a plurality of caregivers over a globally secure communications network. Method 300 may be implemented using one or more processors (e.g., processor 403 of FIG. 4).

At step 301, the processor may receive a medical diagnostic associated with a patient having a plurality of caregivers. For example, an X-ray image, CT scan, heartbeat monitor, or other output of a medical device and/or test may be received by the processor for secure storage. Based on the associated patient, the processor may determine one or more caregivers associated with the patient.

At step 303, the processor may verify, using devices associated with the plurality of caregivers, that locations associated with the plurality of caregivers are within an approved area. For example, the verification for each caregiver may be performed similar to steps 203 and/or 211 of method 200, described above.

At step 305, the processor may verify credentials of the plurality of caregivers. For example, the verification for each caregiver may be performed similar to steps 205 and/or 213 of method 200, described above.

At step 307, the processor may automatically transmit an update including the medical diagnostic to verified caregivers. For example, the update may comprise a chat message including the new diagnostic or a link to view the new diagnostic sent to an application on user interface devices associated with the plurality of caregivers. In some embodiments, the application may be configured to receive encrypted chat messages and therefore preserve the secrecy of the medical diagnostic being transmitted.

By way of further example, the update may comprise a push notification for the user interface devices. In some embodiments, push notification may hide sensitive information until the caregiver unlocks the associated user interface device. For example, the push notification may simply state, "A patient has a new X-ray image" or "There is new information about a patient." Such notifications may preserve the secrecy of the medical diagnostic in case others view a lock screen of a user interface device associated with a caregiver.

In embodiments having hidden information (such as a push notification without the full diagnostic, a chat message without the full diagnostic, and/or a link that the user must activate to receive the full diagnostic), the processor may further verify of the credentials of the caregiver prior to displaying and/or transmitting the hidden information. In some embodiments, then, the processor may skip step 305 and verify the credentials of the plurality of caregivers on an on-demand basis. In other embodiments, the processor may execute step 305 and thereafter verify the credentials of the plurality of caregivers on an on-demand basis. Similar embodiments apply, whether separately or in combination, to the locations of the plurality of caregivers.

At step 309, the processor may withhold the update from caregivers that were not verified. Method 300 may include additional steps. For example, after step 309, the processor may retain a list of caregivers that were not verified. In some embodiments, method 300 may further include monitoring locations and/or credentials of caregivers on the list. For example, the processor may then verify a caregiver on the list at a later time using an updated location and/or credentials and then transmit the update to the caregiver verified at a later time. In such an example, the caregiver may then be removed from the list after receiving the update.

In embodiments where the process retains the list, method 300 may alternatively or additional include receiving, from a caregiver on the list, the updated location and/or credentials along with a request for pending updates. In response to the request, the processor may verify the caregiver on the list using the updated location and/or credentials and then transmit the update to the caregiver in response to the request. In such an example, the caregiver may then be removed from the list after receiving the update.

In embodiments where the process retains the list, the retained list may have an expiry date and/or time, as explained above. Accordingly, method 300 may include clearing (or otherwise deleting) the list when the expiry date and/or time is reached. Additionally, or alternatively, the retained list may expire when the associated patient is discharged. Accordingly, method 300 may further include clearing (or otherwise deleting) the list after receiving an indication that the associated patient has been discharged.

Figure 4:
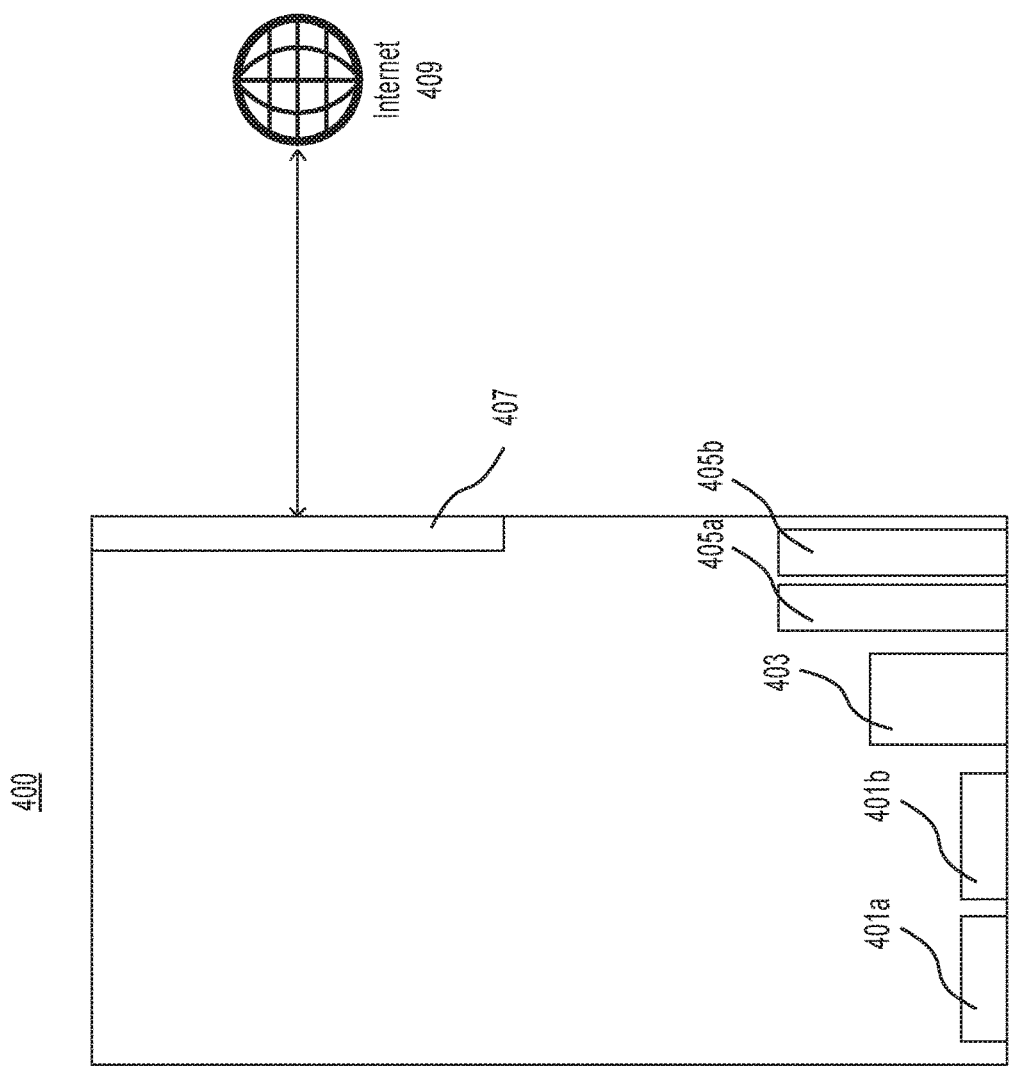
FIG. 4 is a block diagram of an example server with which the systems, methods, and apparatuses of the present invention may be implemented.

FIG. 4 is block diagram of an example device suitable for implementing the disclosed systems and methods. Device 400 may comprise a server, desktop computer, or the like.

As depicted in FIG. 4, example server 400 may include at least one processor (e.g., processor 403) and at least one memory (e.g., memories 405a and 405b).

Processor 403 may comprise a central processing unit (CPU), a graphics processing unit (GPU), or other similar circuitry capable of performing one or more operations on a data stream. Processor 403 may be configured to execute instructions that may, for example, be stored on one or more of memories 405a and 405b.

Memories 405a and 405b may be volatile memory (such as RAM or the like) and/or non-volatile memory (such as flash memory, a hard disk drive, or the like). As explained above, memories 405a and 405b may store instructions for execution by processor 403.

As further depicted in FIG. 4, server 400 may include at least one network interface controller (NIC) (e.g., NIC 407). NIC 407 may be configured to facilitate communication over at least one computing network (e.g., network 409, which is depicted in the example of FIG. 4 as the Internet). Communication functions may thus be facilitated through one or more NICs, which may be wireless and/or wired and may include an Ethernet port, radio frequency receivers and transmitters, and/or optical (e.g., infrared) receivers and transmitters. The specific design and implementation of the one or more NICs depend on the computing network 409 over which server 400 is intended to operate. For example, in some embodiments, server 400 may include one or more wireless and/or wired NICs designed to operate over a GSM network, a GPRS network, an EDGE network, a Wi-Fi or WiMax network, and a Bluetooth® network. Alternatively, or concurrently, server 400 may include one or more wireless and/or wired NICs designed to operate over a TCP/IP network.

As depicted in FIG. 4, server 400 may include and/or be operably connected to one or more storage devices, e.g., storages 401a and 401b. Storage devices 401a and 401b may be volatile (such as RAM or the like) or non-volatile (such as flash memory, a hard disk drive, or the like).

Processor 403, memories 405a and 405b, NIC 407, and/or storage devices 401a and 401b may comprise separate components or may be integrated in one or more integrated circuits. The various components in server 400 may be coupled by one or more communication buses or signal lines (not shown).

Each of the above identified instructions and applications may correspond to a set of instructions for performing one or more functions described above. These instructions need not be implemented as separate software programs, procedures, or modules. Disclosed memories may include additional instructions or fewer instructions. Furthermore, various functions of server 400 may be implemented in hardware and/or in software, including in one or more signal processing and/or application specific integrated circuits.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented with hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive.

Instructions or operational steps stored by a computer-readable medium may be in the form of computer programs, program modules, or codes. As described herein, computer programs, program modules, and code based on the written description of this specification, such as those used by the processor, are readily within the purview of a software developer. The computer programs, program modules, or code can be created using a variety of programming techniques. For example, they can be designed in or by means of Java, C, C++, assembly language, or any such programming languages. One or more of such programs, modules, or code can be integrated into a device system or existing communications software. The programs, modules, or code can also be implemented or replicated as firmware or circuit logic.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. A system for integrating a globally secure communications network with stored medical diagnostics, comprising:
   at least one memory storing instructions; and
   at least one processor configured to execute the instructions to:

establish an approved area for receipt of requests that
  require a secure communication channel for trans-
  mission by establishing at least a geofence surround-
  ing an area identified as an approved location,
  wherein the establishing the geofence comprises
  establishing a plurality of portions of the geofence,
  wherein establishing one of the plurality of portions
  comprises establishing, utilizing a mobile device
  within the vehicle, a mobile portion surrounding a
  vehicle and wherein the establishing the mobile
  portion comprises dynamically changing a size of the
  mobile portion with respect to the vehicle based
  upon one or more real-time factors of the vehicle;
receive, at one or more processors controlling access to
  stored medical data and from a user interface device, a
  request for a medical diagnostic contained within the
  stored medical data, wherein the medical diagnostic is
  stored remotely from a user originating the request,
  wherein the medical diagnostic comprises medical
  information subject to confidentiality requirements and
  that require the secure communication channel for
  transmission to the user;
ensure the secure communication channel for transmis-
  sion of the medical diagnostic to the user interface
  device of the user, wherein to ensure comprises:
  verifying that the request originates from a location
    within the approved area by comparing data sent
    from the user interface device and indicative of a
    location of the user interface device to location
    information of the approved areas; and
  verifying credentials of the user;
send, responsive to ensuring the secure communication
  channel and over the secure communication channel,
  the medical diagnostic to the user;
generate, responsive to receiving a new medical diagnos-
  tic related to the medical diagnostic, an update com-
  prising the new medical diagnostic;
transmit a notification of the update to the user interface
  device of the user, wherein the notification hides sen-
  sitive information included within the new medical
  diagnostic;
display, responsive to verifying the user interface device
  is currently located within the approved area and
  reverifying the credentials of the user, the new medical
  diagnostic including the sensitive information included
  within the new medical diagnostic on the user interface
  device;
receive, from the user, an identification of a recipient for
  the medical diagnostic and the update and in a location
  separate from the user;
ensure a second secure communication channel for trans-
  mission of the medical diagnostic from the user to the
  recipient, wherein to ensure comprises:
  verifying that the identification was sent from a loca-
    tion within the approved area;
  verifying a location of the recipient is within the
    approved area; and
  verifying credentials of the recipient; and
send, responsive to ensuring the second secure commu-
  nication channel and over the second secure commu-
  nication channel, the medical diagnostic and the update
  to the recipient.

2. The system of claim 1 wherein the credentials of the user are verified using credential-based authentication.

3. The system of claim 1 wherein the credentials of the user are verified using role-based authentication.

4. The system of claim 1 wherein the credentials of the recipient are verified using credential-based authentication.

5. The system of claim 1 wherein the credentials of the recipient are verified using role-based authentication.

6. The system of claim 1 wherein the approved area is an area in a medical campus.

7. The system of claim 1 wherein the user and the recipient are in separate approved areas.

8. The system of claim 1 wherein the recipient comprises a plurality of caregivers.

9. A system for automatically updating a plurality of caregivers over a globally secure communications network, comprising:
  at least one memory storing instructions; and
  at least one processor configured to execute the instruc-
    tions to:
    establish an approved area for receipt of requests that
      require a secure communication channel for trans-
      mission by establishing at least a geofence surround-
      ing an area identified as an approved location,
      wherein the establishing the geofence comprises
      establishing a plurality of portions of the geofence,
      wherein establishing one of the plurality of portions
      comprises establishing, utilizing a mobile device
      within the vehicle, a mobile portion surrounding a
      vehicle and wherein the establishing the mobile
      portion comprises dynamically changing a size of the
      mobile portion with respect to the vehicle based
      upon one or more real-time factors of the vehicle;
    receive, at the at least one processor of the system
      controlling access to stored medical data from a device
      connected to the system, a medical diagnostic associ-
      ated with a patient having a plurality of caregivers,
      wherein the medical diagnostic comprises medical
      information subject to confidentiality requirements and
      that require the secure communication channel for
      transmission to the user;
    ensure the secure communication channel for transmis-
      sion of the medical diagnostic to the plurality of
      caregivers, wherein to ensure comprises:
      receiving, at the at least one processor of the system,
        locations of devices associated with each of the
        plurality of caregivers;
      verifying, using the at least one processor of the sys-
        tem, that the locations associated with each of the
        plurality of caregivers are within the approved area
        by comparing data sent from the devices associated
        with each of the plurality of caregivers and indicative
        of a location of a given of the devices to location
        information of the approved areas;
      receiving, using the at least one processor of the
        system, credentials of each of the plurality of care-
        givers; and
      verifying, using the at least one processor of the sys-
        tem, the credentials of each of the plurality of
        caregivers;
    automatically transmit, responsive to ensuring the secure
      communication channel and over the secure commu-
      nication channel, an update for the patient to the
      devices of verified caregivers, wherein the update is
      generated based upon the medical diagnostic;
    withhold, responsive to being unable to verify at least one
      of a location of one of the plurality of caregivers is
      within an approved area and credentials of the one of
      the plurality of caregivers, the update from a device of
      the at least one of the plurality of caregivers that were
      not verified;

generate, responsive to receiving a new medical diagnostic related to the medical diagnostic, an update comprising the new medical diagnostic;

transmit a notification of the update to devices of the plurality of caregivers, wherein the notification hides sensitive information included within the new medical diagnostic; and display, responsive to verifying each of the devices are currently located within the approved area and reverifying the credentials of each of the plurality of caregivers, the new medical diagnostic including the sensitive information included within the new medical diagnostic on the user interface devices that are verified.

10. The system of claim 9 wherein the credentials of the plurality of caregivers are verified using credential-based authentication.

11. The system of claim 9 wherein the credentials of the plurality of caregivers are verified using role-based authentication.

12. The system of claim 9 wherein the approved area is an area in a medical campus.

13. The system of claim 9 wherein the plurality of caregivers are in separate approved areas.

14. The system of claim 9 wherein the instructions further comprise:
generate a list of caregivers that were not verified;
verify, from the list of caregivers that were not verified, a caregiver at a later time based on an updated location of the caregiver; and
transmit the update to the caregiver verified at a later time.

15. A computer implemented method for automatically updating a plurality of caregivers over a globally secure communications network, comprising:
establishing an approved area for receipt of requests that require a secure communication channel for transmission by establishing at least a geofence surrounding an area identified as an approved location, wherein the establishing the geofence comprises establishing a plurality of portions of the geofence, wherein establishing one of the plurality of portions comprises establishing, utilizing a mobile device within the vehicle, a mobile portion surrounding a vehicle and wherein the establishing the mobile portion comprises dynamically changing a size of the mobile portion with respect to the vehicle based upon one or more real-time factors of the vehicle;
receiving, at a processor of a system controlling access to stored medical data from a device connected to the system, a medical diagnostic associated with a patient having a plurality of caregivers, wherein the medical diagnostic comprises medical information subject to confidentiality requirements and that require the secure communication channel for transmission to the user;
ensuring the secure communication channel for transmission of the medical diagnostic to the plurality of caregivers, wherein the ensuring comprises:
receiving, at the processor of the system, locations of devices associated with each of the plurality of caregivers;
verifying, using the at least one processor of the system, that the locations associated with each of the plurality of caregivers are within the approved area by comparing data sent from the devices associated with each of the plurality of caregivers and indicative of a location of a given of the devices to location information of the approved areas;
receiving, using the processor of the system, credentials of each of the plurality of caregivers; and
verifying, using the processor of the system, the credentials of each of the plurality of caregivers;
automatically transmitting, responsive to ensuring the secure communication channel and over the secure communication channel, responsive to being unable to verify at least one of a location of one of the plurality of caregivers is within the approved area and credentials of the one of the plurality of caregivers wherein the update is generated based upon the medical diagnostic;
withholding, responsive to being unable to verify at least one of a location of one of the plurality of caregivers is within the approved area and credentials of the one of the plurality of caregivers, the update from a device of the at least one of the plurality of caregivers that were not verified;
generating, responsive to receiving a new medical diagnostic related to the medical diagnostic, an update comprising the new medical diagnostic;
transmitting a notification of the update to devices of the plurality of caregivers, wherein the notification hides sensitive information included within the new medical diagnostic; and
displaying, responsive to verifying each of the devices are currently located within the approved area and reverifying the credentials of each of the plurality of caregivers, the new medical diagnostic including the sensitive information included within the new medical diagnostic on the user interface devices that are verified.

16. The method of claim 15 wherein the credentials of the plurality of caregivers are verified using credential-based authentication.

17. The method of claim 15 wherein the credentials of the plurality of caregivers are verified using role-based authentication.

18. The method of claim 15 wherein the approved area is an area in a medical campus.

19. The method of claim 15 wherein the plurality of caregivers are in separate approved areas.

20. The method of claim 15 further comprising:
generating a list of caregivers that were not verified;
verifying, from the list of caregivers that were not verified, a caregiver at a later time based on an updated location of the caregiver; and
transmitting the update to the caregiver verified at a later time.

* * * * *